US008282548B2

(12) United States Patent
Kelner (10) Patent No.: US 8,282,548 B2
(45) Date of Patent: Oct. 9, 2012

(54) SURGICAL TISSUE RETRACTOR (76) Inventor: Roman Kelner, Northbrook, IL (US)

( * ) Notice: Subject to any disclaimer, the term of this patent is extended or adjusted under 35 U.S.C. 154(b) by 931 days.

(21) Appl. No.: 12/271,482

(22) Filed: Nov. 14, 2008

(65) Prior Publication Data
US 2010/0125171 A1 May 20, 2010

(51) Int. Cl.
*A61B 1/32* (2006.01)

(52) U.S. Cl. ........................................ 600/210; 600/214

(58) Field of Classification Search .................. 600/201, 600/205, 210, 214, 220, 226, 206, 237, 239, 600/240, 242; 433/93; 128/200.15, 860
See application file for complete search history.

(56) References Cited

U.S. PATENT DOCUMENTS

| 487,873 | A | * | 12/1892 | Blackman | 128/200.15 |
|---|---|---|---|---|---|
| 2,831,480 | A | * | 4/1958 | Milano | 600/242 |
| 4,481,947 | A | * | 11/1984 | Chester | 600/210 |
| 4,686,972 | A | * | 8/1987 | Kurland | 600/210 |
| 4,945,896 | A | * | 8/1990 | Gade | 600/206 |
| 5,143,054 | A | * | 9/1992 | Adair | 600/221 |
| 5,351,680 | A | * | 10/1994 | Jung | 600/214 |
| 5,730,597 | A | * | 3/1998 | Luttrell | 600/237 |
| D523,142 | S | * | 6/2006 | Stalcup et al. | D24/135 |
| 2009/0043169 | A1 | * | 2/2009 | Trieu et al. | 600/220 |
| 2009/0216089 | A1 | * | 8/2009 | Davidson | 600/235 |

* cited by examiner

*Primary Examiner* — Brian E. Pellegrino
(74) *Attorney, Agent, or Firm* — Wood, Phillips, Katz, Clark & Mortimer (57) ABSTRACT

Novel ergonomically designed hand held surgical tissue Z-shaped retractors. The retractors include retractor plates which are angulated and deviated from the main axis along the handle of the retractor. The retractors may be applicable for general, cosmetic and reconstructive surgeries, cardio, vascular, obstetrics/gynecology applications, and veterinary practices.

12 Claims, 10 Drawing Sheets

FOLDS IN FABRIC (8) PLACES EQUALLY SPACED TO CREATE POUCH

STITCHING ALONG (2) EDGES TO SECURE FOLDS

Fig. 10b

FOLDS IN FABRIC (8) PLACES EQUALLY SPACED TO CREATE POUCH

STITCHING ALONG (2) EDGES TO SECURE FOLDS

PERFORATION IN FABRIC USED TO SEPARATE HALVES AND REMOVE GUARD AFTER IMPLANT IS IN PLACE

SURGICAL TISSUE RETRACTOR

FIELD OF THE INVENTION

The invention generally relates to novel surgical instruments, including ergonomically designed hand held surgical tissue retractors and a pouch for breast implants. The invention also relates to novel methods of performing surgical operations, in particular, cosmetic and reconstructive surgery using inflatable and pre-filled breast enlargement implants. Retractors and methods of the invention may also be applicable for general, orthopedic, cardio, vascular, microsurgeries, obstetrics/gynecology applications, and veterinary practices.

BACKGROUND OF THE INVENTION

There are three major types of implants commonly used for breast enlargement surgeries: a) saline filled or inflatable breast implants, b) saline pre-filled implants, and c) silicone gel pre-filled implants (also called pre-shaped breast enlargement implants). Saline filled breast implants are constructed from room temperature vulcanized (RTV) silicone elastomer, made of polydimethylsiloxane. Silicone gel pre-filled implants are pre-filled by silicone gel and sealed by a manufacturer.

A breast implant's shell is not a monolithic monolayer; rather, it is made up from several layers of "hardening" silicone. Thickness of the shell is measured in "deeps", which refers to the number of times the process is repeated. An average breast implant is between 4 and 6 "deeps" thick.

Accordingly, the technology used to prepare implants results in a multilayered shell's structure. Further, each layer is not evenly "deep" throughout different parts of the implant's surface. The implantation process involves putting pressure on the implant's shell, causing its distention and deformation. As a result, microseparations may form in the layers, weakening the whole shell's structure. The microseparations also decrease the resistance of the implant's shell to hydrostatic pressure and to the gravity force. Over time, this may result in the penetration of silicone through the implant's shell ("bleeding") and may increase the potential for disruption and/or leakage.

There is a lot of potential for damage to the implant during its placement into a patient's body. There are four different access incision sites for breast enlargement surgeries: inframammary, transareolar, transaxillary, and transumbilical incisions. Inframammary, transareolar, and transaxillary incisions are used to place saline inflatable and saline and silicone filled pre-shaped implants. Saline inflatable implants are commonly filled with a sterile 0.9% sodium chloride solution either inside or outside the patient's body. Silicone filled implants are filled to a certain volume and sealed by manufacturer.

Transumbilical incision is a less common technique, where an incision is made on the rim of the navel. A tunnel is then made under the skin through the subcutaneous fat layer. An endoscope can be used to create the tunnel and to provide visibility to the surgeon. The tunnel reaches all the way beneath the mammary gland into the layer of tissue in between the breast and pectoral muscles. After a pocket is created under the breast, the implant is inserted through the incision and moved up into the breast area. The implant is then centered behind the nipple. This approach enables implants to be placed with no visible scars on the breast, but makes appropriate dissection and implant placement more difficult. This technique is not appropriate for placing silicone gel and saline pre-filled implants due to potential damage of the implant shell during blunt insertion and long and narrow passage.

There are two primary anatomical positions for permanent placement of breast implants in the body: subglandular and subpectoral. In subglandular breast implant placement, the implants are placed behind the mammary gland and over the chest wall muscles (pectoral major, pectoral minor muscles and pectoral fascia). In subpectoral implant placement, the implants are placed beneath the breast glands and under the chest wall muscles, and anterior to the rib cage. In either method, symmetrical pockets are surgically formed between the described above anatomical structures prior to the placement of any type of breast enlargement implants.

Saline inflatable breast implants are completely deflated outside of the patient's body. When they are inserted in the human body through small skin incisions (about 2.5 to 4.0 cm long), they are rolled in toward the filling valve. Once the deflated implant is placed into the preformed pocket, it is filled with sterile 0.9% sodium chloride solution, up to a designated volume, using one of the preferred breast implants filling kits. The self sealed valve (or plug) is designed to seal the implant's saline content.

Different approaches and techniques are used to place pre-filled saline or silicone filled gel implants. Pre-filled saline or silicone breast implants possess much larger cross sectional dimensions before implantation as compared to deflated inflatable saline implants. Many surgeons prefer to fill inflatable saline implants outside of the patient's body before implantation to observe their shape, size, and to ensure the proper valve closure. Significantly longer skin incisions (from 6.0 cm to 8.0 cm long) and wider dissection of the local tissue are needed to accommodate the passage of pre-filled breast implants and their implantation.

Surgical retractors, for example, Army/Navy or Deaver-type retractors are commonly used to provide incision opening and directional passage for the implant's placement. In the process of placement, a surgeon positions the pre-filled breast implant next to the incision site and then pushes one of the implant's edges inside the retracted incision, while holding the "body" of the implant outside of the incision, preventing it from slipping out of the incision and reassuring the mono-directional movement of the implant into the placement pocket. Usually, the first assistant is keeping the incision site retracted as much as possible, and thus prevents the collapse of the formed placement pocket. During this process, the surgeon places a lot of pressure on the implant to force it into the placement pocket, protruding its mass up to 4.0 to 6.0 cm deep, repeating the process multiple times until all of the implant is successfully placed inside. This implantation method causes a great deal of destructive stress and distention on the implant's shell layers, weakening the shell layers integrity.

The transareolar incision results in scars which are more cosmetically acceptable but it limits the skin incision's length. However, the implant is under a lot of stress when this technique is used. The tissue at the incision area is more resistant to dissections. Further, the implant's passing tunnel has a complex, angled pattern. Thus, transareolar access requires applying more pressure on the shaped implant and creating more local tissue dissections in the process of placement.

The placement of the pre-filled implant through the transaxillary incision is even more complex. The initial part of the implantation tunnel passes under the thickest part of the pectoral major muscle, and the implantation passage has an oblique, caudal, and medially directed path. The incision length is limited by the length of axillary folds. Army/Navy type or Deaver-type retractors are commonly used to maintain a sufficient perimeter of the incision and prevent collapse of the passage. The pre-tilled breast implants are under the pressure from the surgeon's manipulations directed to advance forward segments of the implant, and resistance of the local tissue and anatomical structures. Thus, the process of implant's placement is rather complicated. When the implant is pushed and compressed to force a part of it go inside of the incision or implantation passage, distention of the shell's capsule occurs.

Further, there is a lot of air trapped inside the placement pocket. This air becomes progressively compressed as the implant advances toward the placement pocket, and the air pressure inside the passage rapidly increases. The compressed air resists the implant's advancement and forces the surgeon to apply extra force to overcome the air's resistance. The mechanical pressure resulting from the surgeon's protruding the implant further damages the implant's shell layers and weakens the layers' integrity.

Currently known retractors commonly used in breast enhancement surgeries result in unbalanced and uneven physical pressure, which contributes to the implant's damage during the surgery. Unbalanced physical pressure, applied to the local anatomical structures, causes trauma to the local fat tissue, muscle fibers, nerve endings, lymphatic, and milk ducts, and results in more pain after the surgery, contribute to development of excessive scar formation, and capsule contraction.

Some of the conventional approaches to overcoming these problems involve increasing the incisions' length and making more and wider local tissue dissections along the implantation passage. However, these approaches are themselves deficient since longer incisions and more local tissue dissections are leading to intra operational and post surgical complications such as bleeding, local fat necrosis, breast itself and nipple's lack of sensation, skin irregularities, slow healing, explantations, infection, capsule contraction, and keloid formation.

Accordingly, it would be desirable to provide improved techniques of performing breast implantations by pre-filled implants. It would also be desirable to provide new and improved surgical instruments, such as new and improved retractors.

BRIEF SUMMARY OF THE INVENTION

In one embodiment, the present invention provides a retractor for use in surgical procedures wherein said retractor comprises:
  a handle, wherein said handle comprises at least two compartments suitable for a suction tube;
  a first retractor plate contiguous to said handle, wherein said first retractor plate is curved at an angle of between about 20° and about 40° along the Y-axis to said handle, and at an angle of between about 25° and about 45° along the X-axis to said handle; and
  a second retractor plate contiguous to said handle, wherein said second retractor plate is curved at the opposite end of said handle at an angle of between about 20° and about 40° along the Y-axis to said handle, and at an angle of between about 25° and about 45° along the X-axis to said handle, and wherein said second retractor plate is curved in the opposite direction to said first retractor plate relative to said handle.

In a preferred embodiment, the handle of the retractor is between about 140 mm and about 180 mm in length; between about 20 mm and about 40 mm in width; and between about 0.5 mm and about 1.5 mm thick.

Most preferably, the handle of the retractor is about 160 mm in length, about 30 mm in width, and about 1 mm thick.

In another preferred embodiment, the first retractor plate is between about 40 mm and about 60 mm in length; between about 20 mm and about 40 mm in width; and between about 0.5 mm and about 1.5 mm thick.

Most preferably, the first retractor plate is about 50 mm in length; about 30 mm in width, and about 1 mm thick.

In another preferred embodiment, the second retractor plate is between about 25 mm and about 45 mm in length; between about 16 mm and about 36 mm in width; and between about 0.5 mm and about 1.5 mm thick.

Most preferably, the second retractor plate is about 35 mm in length, about 26 mm in width, and about 1 mm thick.

In yet another embodiment, the invention provides another retractor for use in surgical procedures, wherein said retractor comprises a handle wherein said handle comprises at least one compartment suitable for a suction tube; and a retractor plate contiguous to said handle, wherein said first retractor plate is curved at an angle of between about 20° and about 40° along the Y-axis to said handle, and at an angle of between about 25° and about 45° along the X-axis to said handle;

In a preferred embodiment, the handle of this second provided retractor is between about 120 mm and about 140 mm in length; between about 16 mm and about 36 mm in width; and between about 0.5 mm and about 1.5 mm thick.

Most preferably, the handle is about 130 mm in length, about 26 mm in width, and about 1 mm thick.

In a preferred embodiments, both provided retractors comprise a plurality of openings to decrease their weight.

Both types of retractors can be made either of a surgical grade stainless steel or of plastic materials; if they are made of plastic materials, they further comprise stainless steel mesh which covers both surfaces of the retractors.

In yet another aspect, both types of retractors may be disposable.

In another aspect, the invention provides a disposable pouch for a breast implant wherein said pouch is made from a synthetic nanotech porous fiber material, wherein said disposable pouch has at least two notches and wherein a perforated line is extended from each of said two notches.

In yet another aspect, the invention provides a surgical kit comprising one or both of the described retractors.

In yet another aspect, the invention provides a method of performing a breast enhancement surgery using pre-filled breast implants, wherein said method comprises the use of one or both of the provided retractors and the use of a suction generating device to create a negative pressure in the placement pocket for the breast implant.

Preferably, the provided method of performing a breast enhancement surgery using pre-filled breast implants comprises the use of the provided disposable pouch for the breast implant.

BRIEF DESCRIPTION OF THE DRAWINGS

FIG. 1a is a rear view of a surgical retractor according to a preferred embodiment of the specification; wherein said surgical retractor further comprises suction tubes.

FIG. 1b is a side view the surgical retractor in FIG. 1a.

FIG. 1c is a front view of the surgical retractor in FIG. 1a.

FIG. 1d is an enlarged view of the distal portion of the first retractor plate of the surgical retractor in FIG. 1a.

FIG. 2b is an enlarged view of the portion of the first retractor plate of the surgical retractor in FIG. 2a.

FIG. 2c is an enlarged view of the distal portion of the second retractor plate of the surgical retractor in FIG. 2a.

FIG. 3b is a side view of the surgical retractor in FIG. 3a.

FIG. 3c is a rear view of the surgical retractor in FIG. 3a.

FIG. 4a is a more detailed front view of the surgical retractor in FIG. 3a.

FIG. 4b is an enlarged view of the distal portion of the first retractor plate of the surgical retractor in FIG. 4a.

FIG. 5a is a front view of another embodiment of the surgical retractor in FIG. 3a.

FIG. 5b is a side view of another embodiment of the surgical retractor in FIG. 3a.

FIG. 5c is a rear view of another embodiment of the surgical retractor in FIG. 3a.

FIG. 6 is a more detailed front view of the surgical retractor in FIG. 5a.

DETAILED DESCRIPTION OF THE INVENTION

In one embodiment, the present invention provides a retractor for use in surgical procedures wherein said retractor comprises:
- a handle, wherein said handle comprises at least two compartments suitable for a suction tube;
- a first retractor plate contiguous to said handle, wherein said first retractor plate is curved at an angle of between about 20° and about 40° along the Y-axis to said handle, and at an angle of between about 25° and about 45° along the X-axis to said handle; and
- a second retractor plate contiguous to said handle, wherein said second retractor plate is curved at the opposite end of said handle at an angle of between about 20° and about 40° along the Y-axis to said handle, and at an angle of between about 25° and about 45° along the X-axis to said handle, and wherein said second retractor plate is not curved in the opposite direction to said first retractor plate relative to said handle.

Figures 1A, 1B:
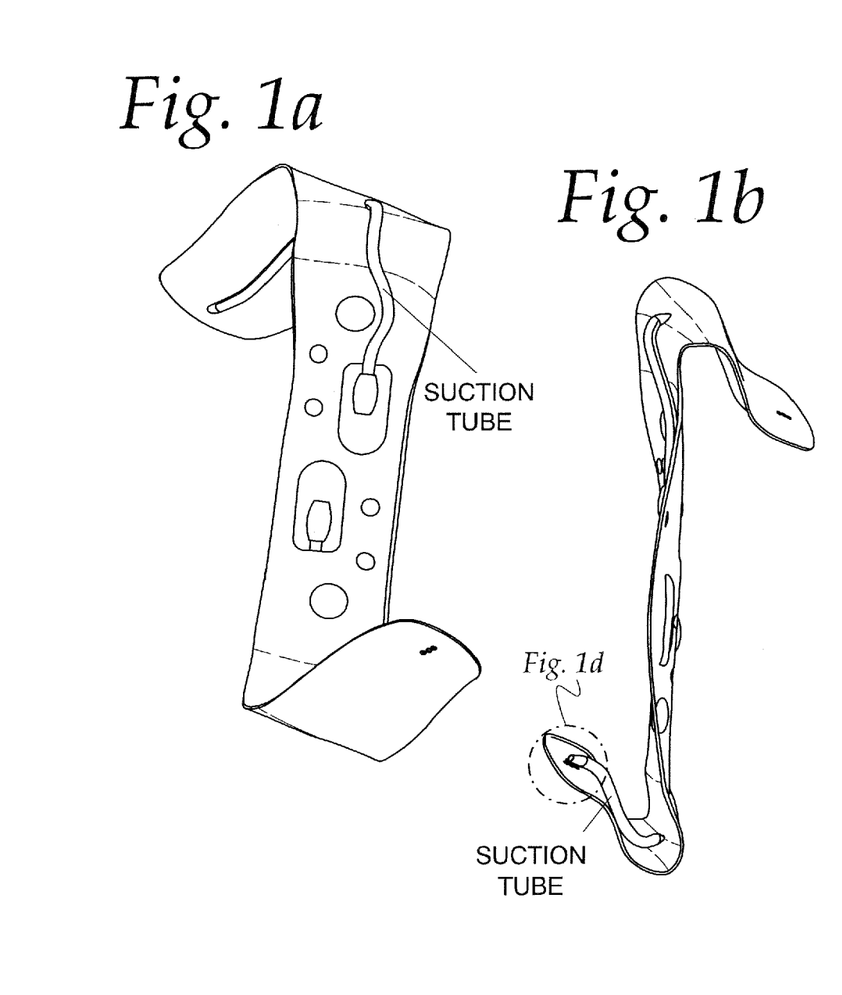
Figures 1C, 1D:
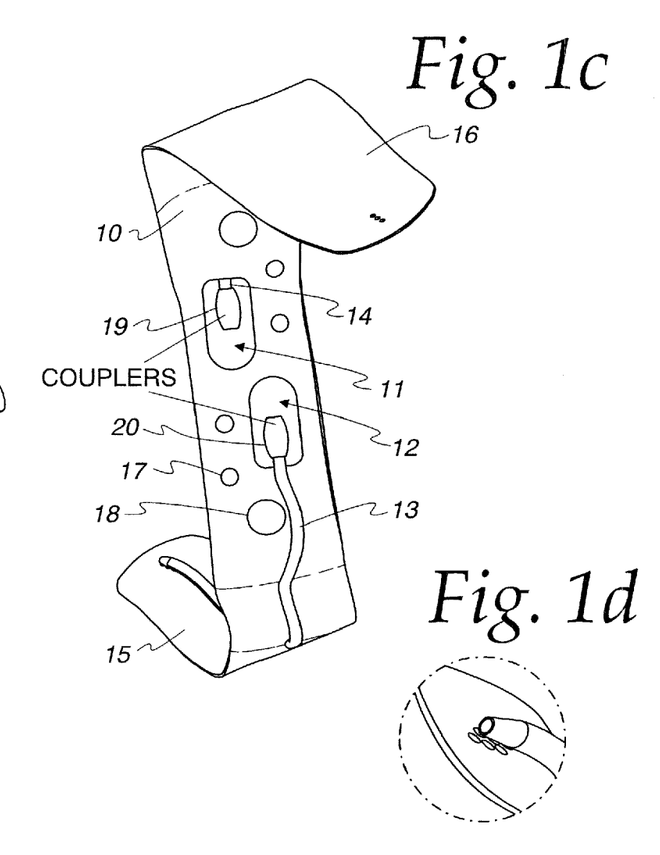
Figure 2A:
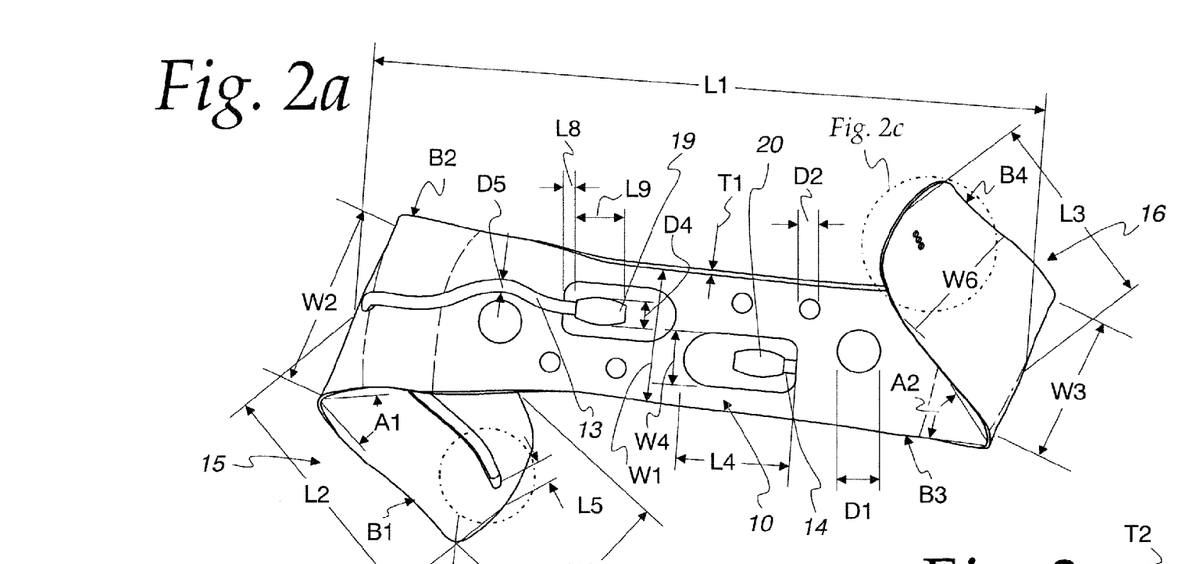
FIG. 2a is a more detailed front view of the surgical retractor in FIG. 1c.
Figure 2B:
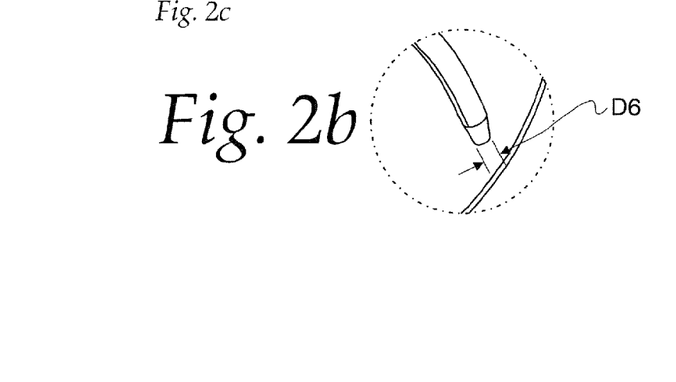
Figure 2C:
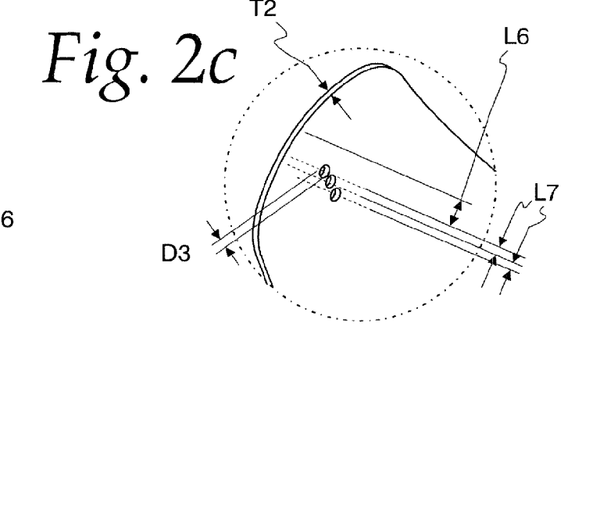

A presently preferred embodiment of the above type of the surgical retractor is illustrated in FIGS. 1-2.

FIG. 1c shows a front view of the surgical retractor. The handle 10 is provided, wherein the handle comprises compartments 11 and 12 suitable for optional suction tubes 13 and 14, respectively. A first retractor plate 15 and a second retractor plate 16 are provided, wherein both retractor plates are contiguous to the handle 10. The surgical retractor optionally includes a plurality of openings 17 and 18. The suction tubes 13 and 14 optionally comprise suction couplers 19 and 20, respectively.

The suction tubes 13 and 14 can be connected to a suction generating device to create a negative pressure in the placement pocket for the breast implant. The suction tubes 13 and 14 may operate independently and separately from each other.

The edges of the retractor may be rounded.

The suction tube 13 or 14 has an elliptical cross section. The suction tube 13 or 14 may be located roughly in the middle of said first retractor plate 15 and/or said second retractor plate 16. Preferably, the suction tube 13 or 14 follows the curvature of the handle 10, penetrates the retractor through an opening to extend onto the inner surface of said first retractor plate 15 and/or said second retractor plate 16. Preferably, the suction tube 13 and/or 14 adds rigidity to the structure of said first retractor plate 15 and/or said second retractor plate 16. The suction tubes 13 and 14 comprise one suction opening. When the retractor is used during a breast enhancement surgery, the suction opening faces the soft tissue of the placement pocket and assures adequate suction from both sides of said first retractor plate 15 and/or said second retractor plate 16. Preferably, the suction tubes 13 and 14 comprise three roughly circular openings, which are preferably about 2.5 mm in diameter each. Preferably, during a breast enhancement surgery, the three roughly circular openings face the cavity of the implant placement pocket, enabling evacuation of the air, fluids, and smoke from the wounds and cavities.

FIGS. 1a and 1b show a rear view and a side view of said retractor, respectively.

FIG. 1d shows an enlarged view of the distal portion of the first retractor plate of the surgical retractor in FIG. 1a.

FIG. 2a shows a more detailed front view of the surgical retractor in FIG. 1c, according to a preferred embodiment of the invention.

As can be seen from FIG. 2a, the handle 10 of the retractor may be slightly curved for an improved grip. It may also comprise suction tubes 13 and/or 14 with or without couplers 19 and 20. It is generally preferred to use couplers to connect the suction tubes to a suction device. The suction tubes include, but are not limited to, industry standard, plastic suction tubes, with the inner diameter of about 6.0 mm.

It is to be understood that when the application refers to the "Z-shaped" retractor, it is referring to the above-described retractor. The provided retractor has a 3-dimensional, Z-shape, comprising retractor plates which are angulated and deviated from the main axis along the handle of the retractor. This shape allows for an extremely convenient placement of the retractor at the incision site. The provided retractor allows considerably more room for manipulation in the surgical field, and is unexpectedly superior to conventional retractors. It allows for a complete opening and retraction of the surgical wound. In a preferred embodiment, during the breast enhancement surgery (such as inframammary, and transareolar, and transaxillary incisions), the retractor handle is not situated straight across the surgeon's field of vision, and thus, it does not restrict the surgeon's view. Further, it does not apply pressure on the nipple since it is located to its side thanks to the side angles between the handle and the retractor plates.

The various dimensions designated with letters in FIG. 2a have preferred values as follows:

The length L1 of the handle 10 is between about 140 mm and about 180 mm; most preferably, about 160 mm.

The angle A between the first retractor plate 15 and the handle 10 along the X-axis (i.e. in the front or rear view of the retractor, to the left or to the right of the handle axis) is between about 25° and about 45°; most preferably, the angle A is about 35°.

The angle B between the second retractor plate 16 and the handle 10 along the Y-axis (i.e. in the side view of the retractor, to the right or to the left of the handle axis) is between about 20° and about 40°; most preferably, about 30°.

The width W1 of the handle 10 is between about 20 mm and about 40 mm; most preferably, about 30 mm.

The thickness T1 of the handle 10 is between about 0.5 mm and about 1.5 mm; most preferably, about 1 mm.

The length L2 of the first retractor plate 14 is between about 40 mm and about 60 mm; most preferably, about 50 mm.

The width W5 of the first retractor plate 14 is between about 20 mm and about 40 mm; most preferably, about 30 mm.

The angle B1 between the distal part of the first retractor plate 14 (the distal part is about 20 mm from each plate's end) and the main axis of the retractor plate 14 is about 10°. The inner diameter D5 of the suction tube 13 and/or 14 is about 5.0 mm.

The diameter D1 of the opening 17 is about 8.0 mm.

The diameter D2 of the opening 18 is about 5.0 mm.

The length L4 of the compartments 11 and 12 is about 34.0 mm.

The width W4 of the compartments 11 and 12 is about 26.0 mm.

The diameter D4 of the opening of the suction couplers 19 and 20 is about 6.0 mm.

The length L3 of the second retractor plate 16 is between about 25 mm and about 45 mm; most preferably, about 35 mm.

The width W6 of the second retractor plate 16 is between about 16 mm and about 36 mm; most preferably, about 26 mm.

FIG. 2b shows an enlarged view of the portion of the first retractor plate of the surgical retractor in FIG. 2a.

FIG. 2c shows an enlarged view of the distal portion of the second retractor plate of the surgical retractor in FIG. 2a.

Figure 3A:
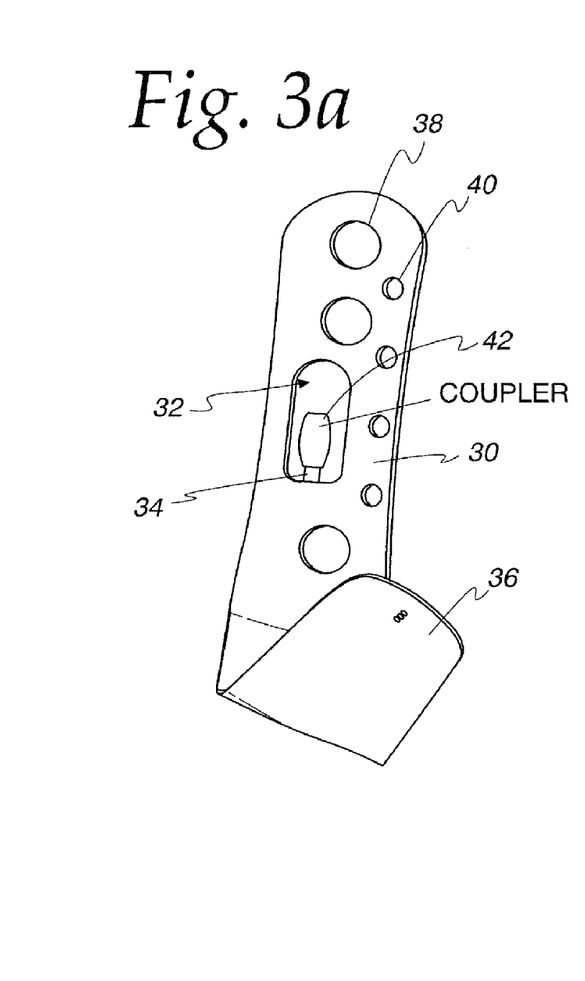
FIG. 3a is a front view of another surgical retractor according to another preferred embodiment of the specification; wherein said surgical retractor further comprises a suction tube.
Figure 3B:
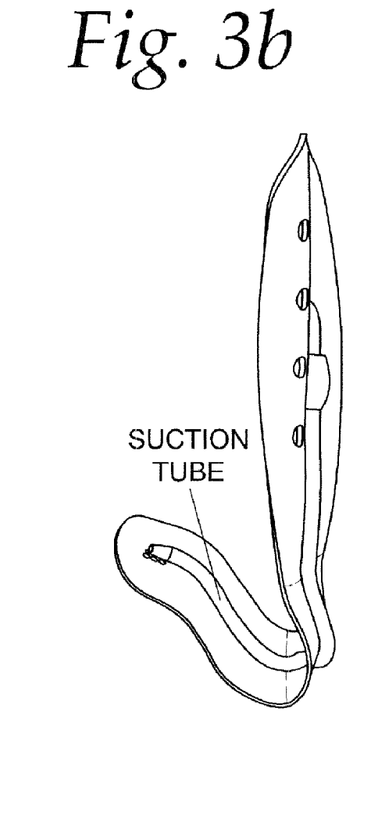
Figure 3C:
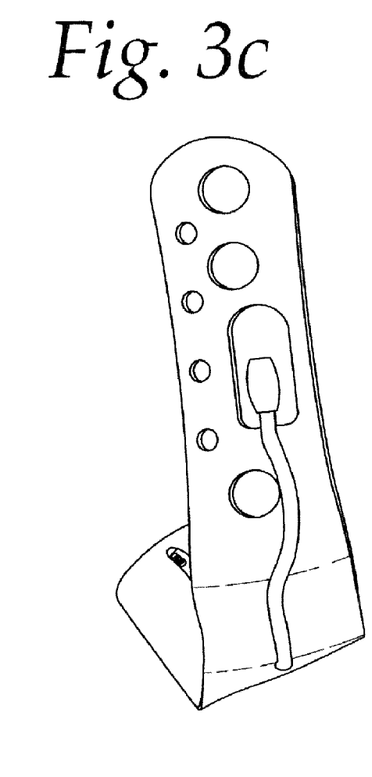

In another embodiment of the present invention, another retractor for use in surgical procedures is provided, wherein said retractor comprises a handle wherein said handle comprises at least one compartment suitable for a suction tube; and a retractor plate contiguous to said handle, wherein said first retractor plate is curved at an angle of between about 20° and about 40° along the Y-axis to said handle, and at an angle of between about 25° and about 45° along the X-axis to said handle;

A presently preferred embodiment of the above type of the surgical retractor is illustrated in FIGS. 3a-3c.

FIG. 3a illustrates a front view, FIG. 3b illustrates a side view, and FIG. 3c illustrates a rear view of the above surgical retractor.

A handle 30 is provided, wherein the handle 30 comprises a compartment 32 suitable for an optional suction tube 34. A retractor plate 36 is provided, wherein the retractor plate 36 is contiguous to the handle 30. The surgical retractor optionally includes a plurality of openings 38 and 40. The suction tube 34 optionally comprises a suction coupler 42.

The suction tube 34 can be connected to a suction generating device to create a negative pressure in the placement pocket for the breast implant.

The edges of the retractor may be rounded.

The location and the structure of the suction tube and of the retractor plate are roughly analogous to the same in the above-described Z-shaped retractor.

It is to be understood that when the application refers to the "singular" retractor, it is referring to the above-described retractor, further illustrated in FIGS. 3-8.

Figures 4A, 4B:
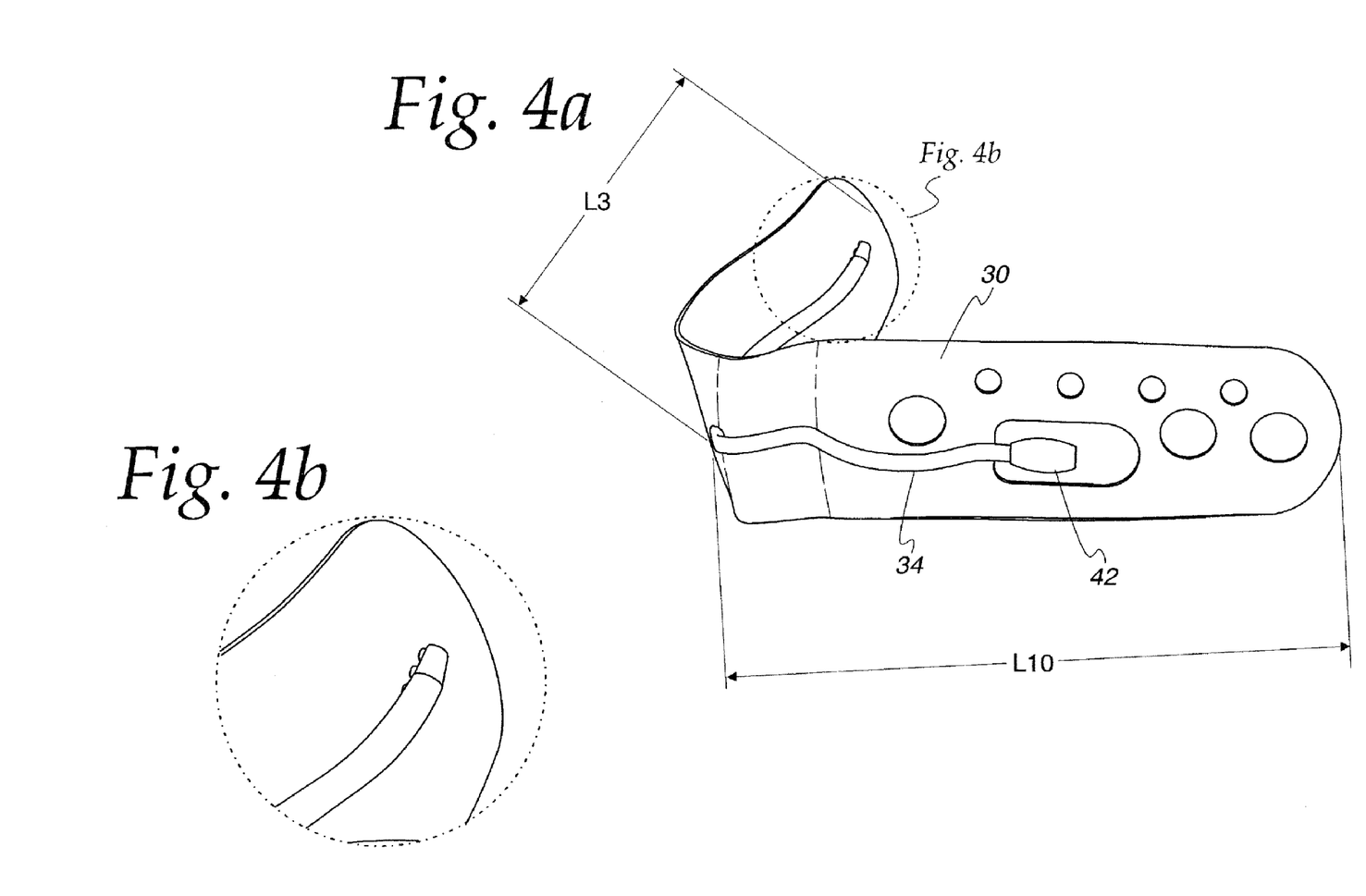
Figure 5A:
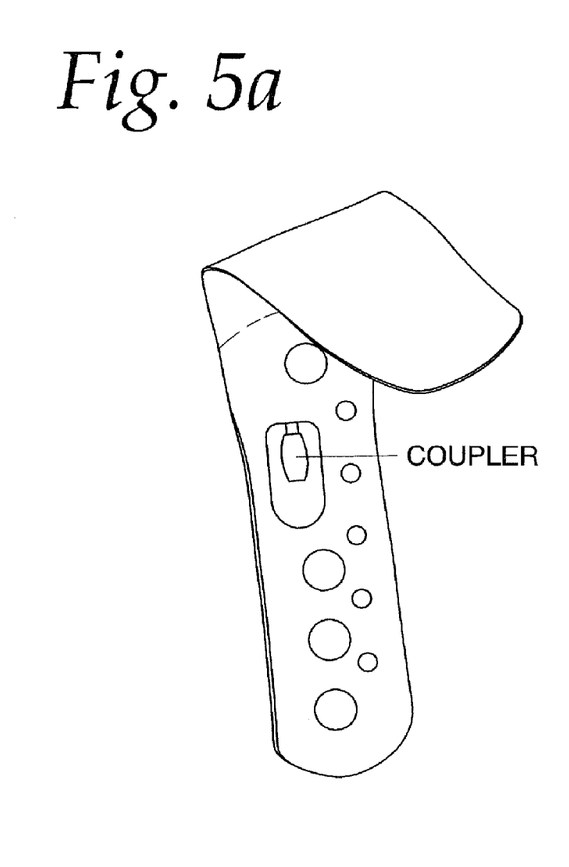
Figures 5B, 5C:
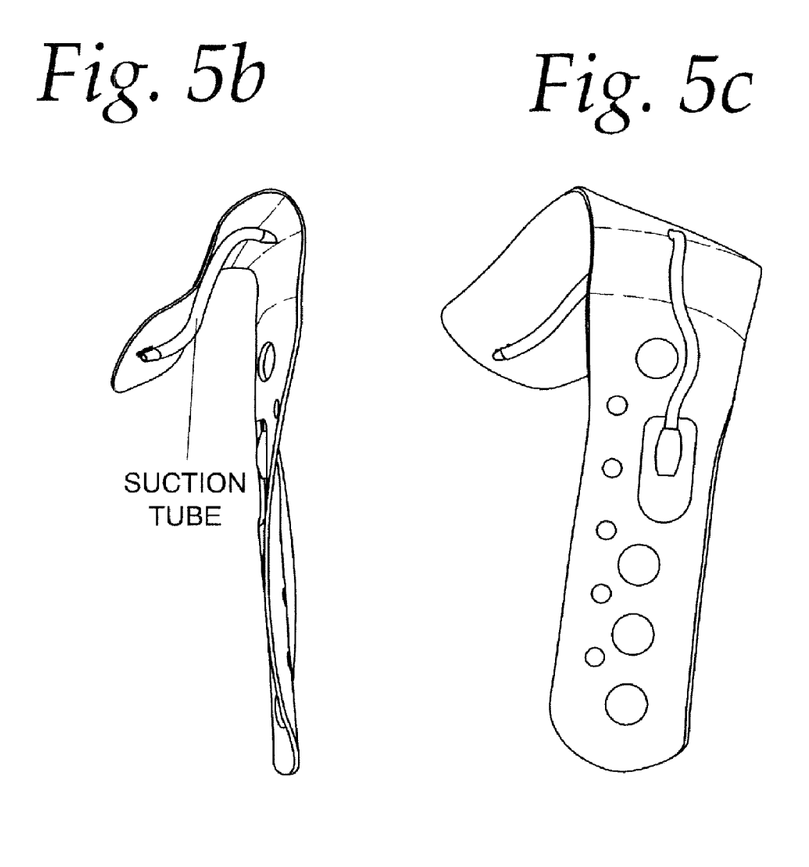
Figure 6:
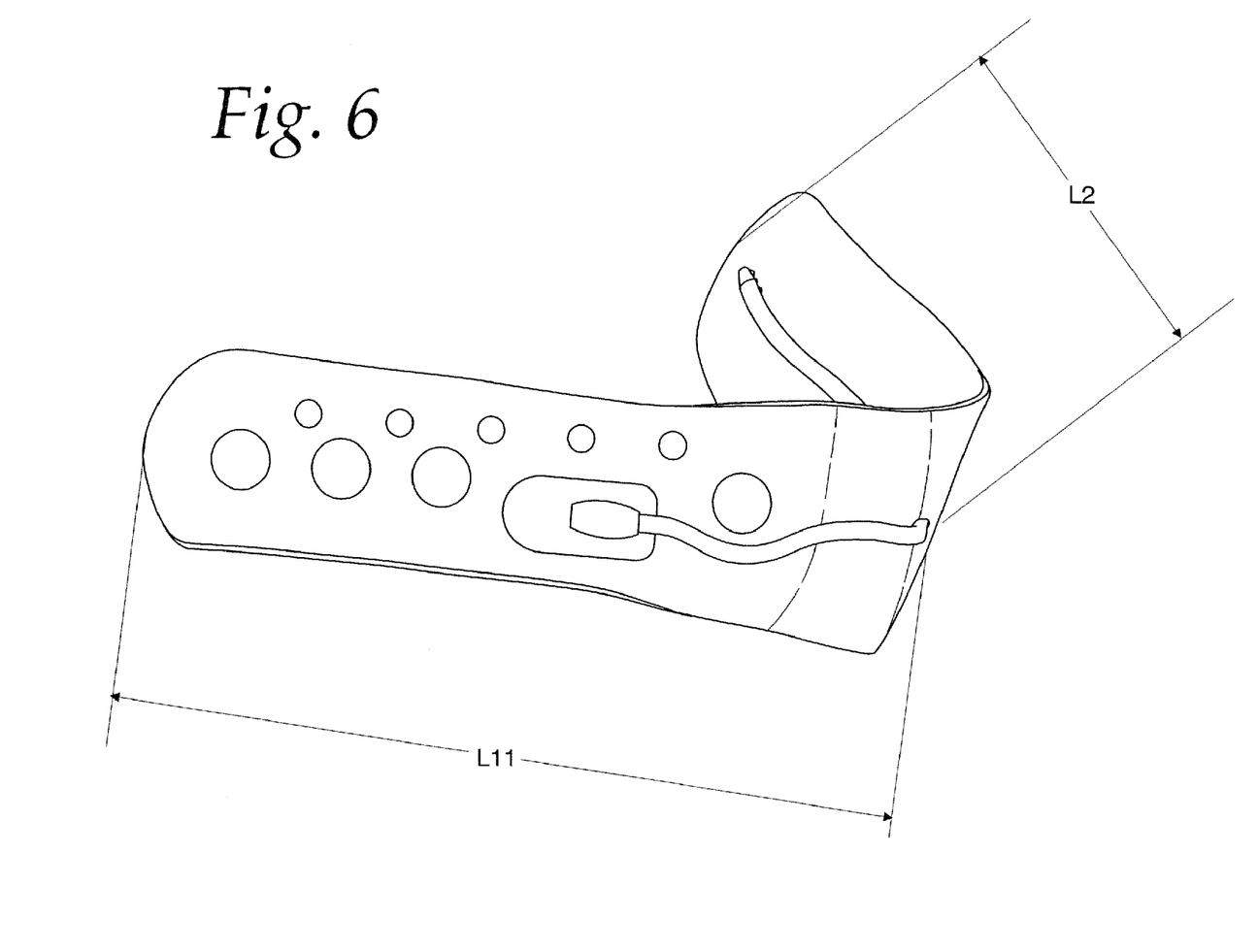
Figure 7A:
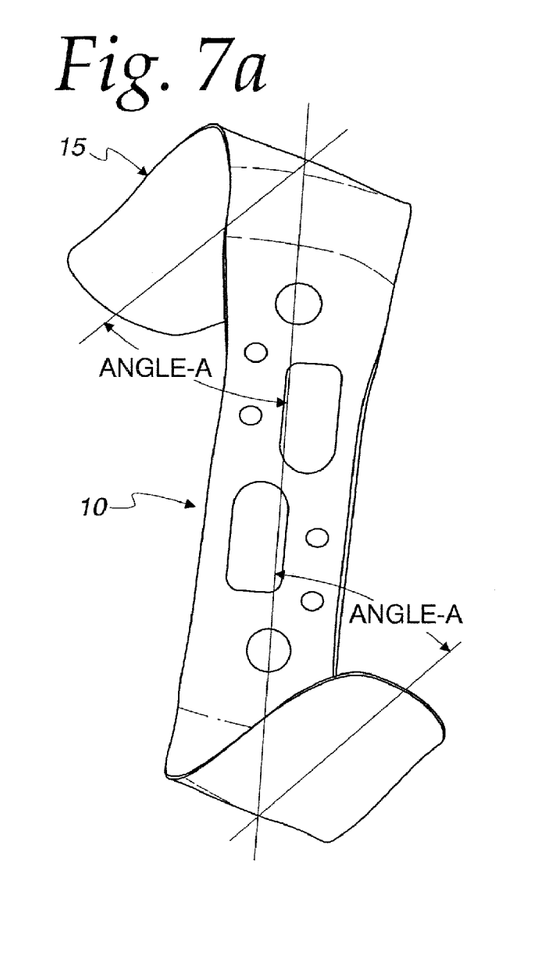
FIG. 7a is a rear view of the surgical retractor in FIG. 1a without suction tubes.
Figure 7B:
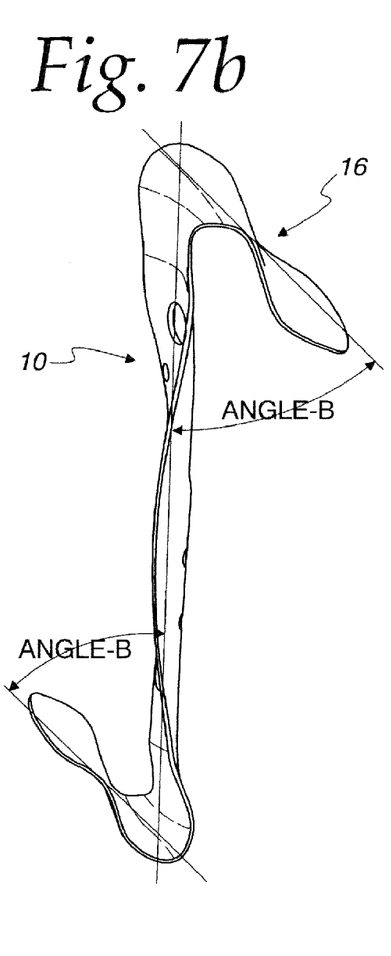
FIG. 7b is a side view of the surgical retractor in FIG. 1a without suction tubes.
Figure 7C:
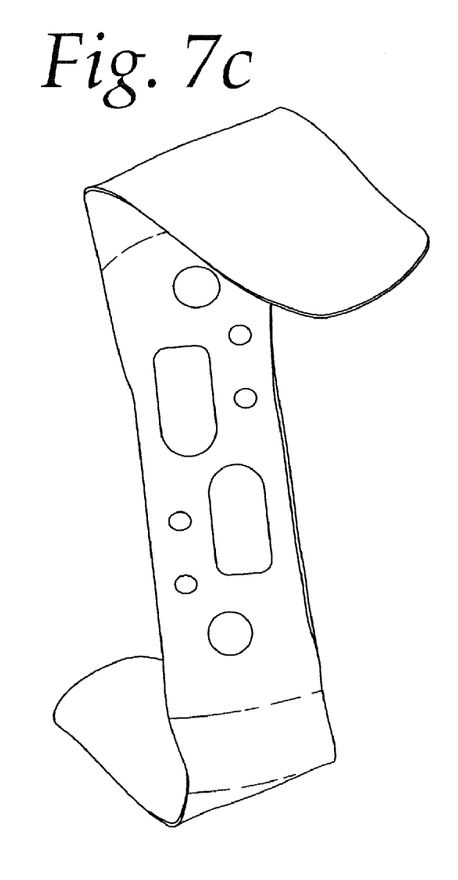
FIG. 7c is a front view of the surgical retractor in FIG. 1a without suction tubes.
Figure 8A:
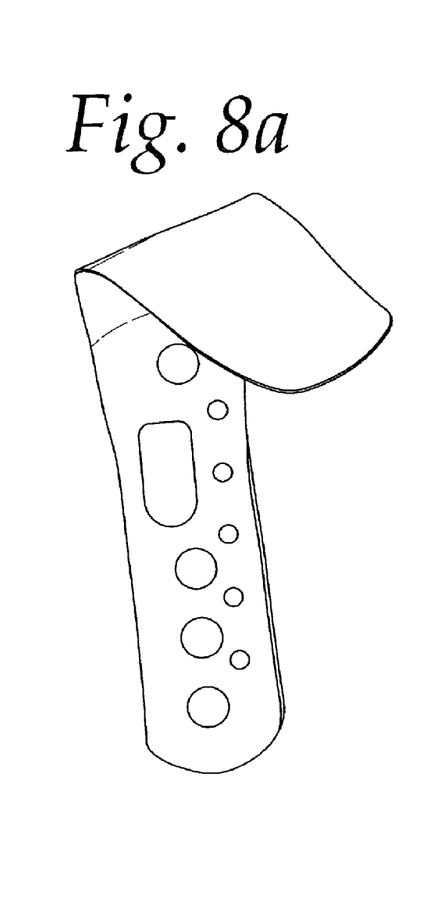
FIG. 8a is a front view of the surgical retractor in FIG. 3a without a suction tube.
Figure 8B:
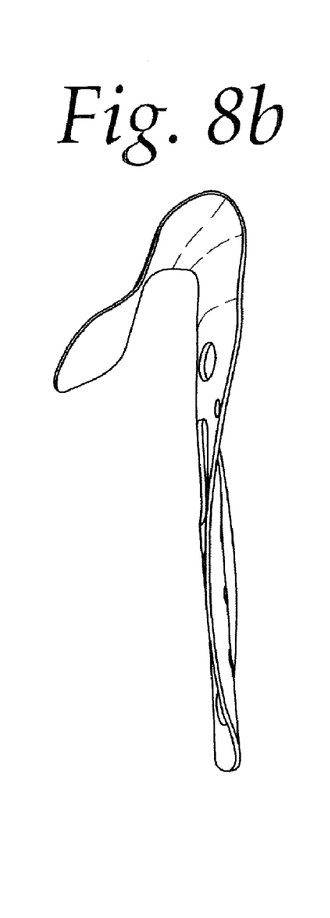
FIG. 8b is a side view of the surgical retractor in FIG. 3a without a suction tube.
Figure 8C:
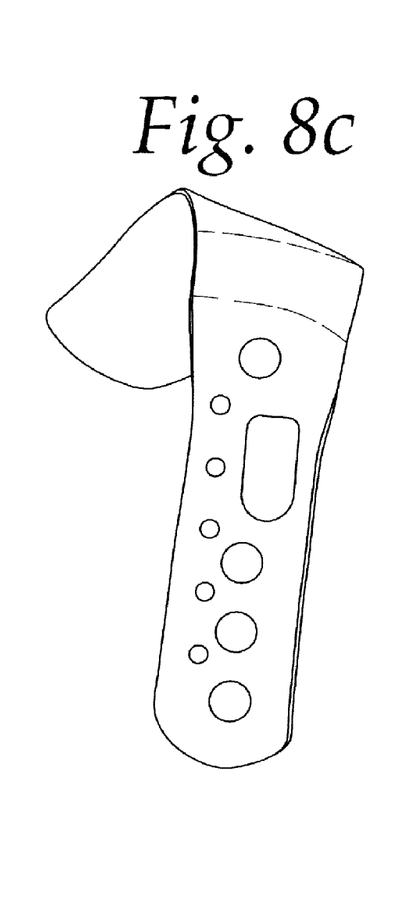
FIG. 8c is a rear view of the surgical retractor in FIG. 3a without a suction tube.

FIG. 4a shows a more detailed front view of the surgical retractor in FIG. 3a, according to a preferred embodiment of the invention.

As can be seen from FIG. 4a, the handle 30 of the retractor may be slightly curved for an improved grip. It may also comprise the suction tube 34 with or without the suction coupler 42.

The various dimensions designated with letters in FIG. 4a have preferred values as follows:

The length L10 of the handle 30 is between about 120 mm and about 140 mm; most preferably, about 130 mm.

The length L3 of the retractor plate 36 is between about 25 mm and about 45 mm; most preferably, about 35 mm.

The width W6 of the retractor plate 36 is between about 16 mm and about 36 mm; most preferably, about 26 mm.

FIG. 4b shows an enlarged view of the distal portion of the first retractor plate of the surgical retractor in FIG. 4a.

In one embodiment, the retractors of the present invention are made of surgical grade stainless steel. Preferably, they are made of titanium alloy. Most preferably, they are made of grade 5 titanium alloy which comprises about 6% aluminum, about 4% vanadium; and about 90% titanium. It is commonly known as Ti6Al4V, Ti-6AL-4V or Ti 6-4.

Figure 9A:
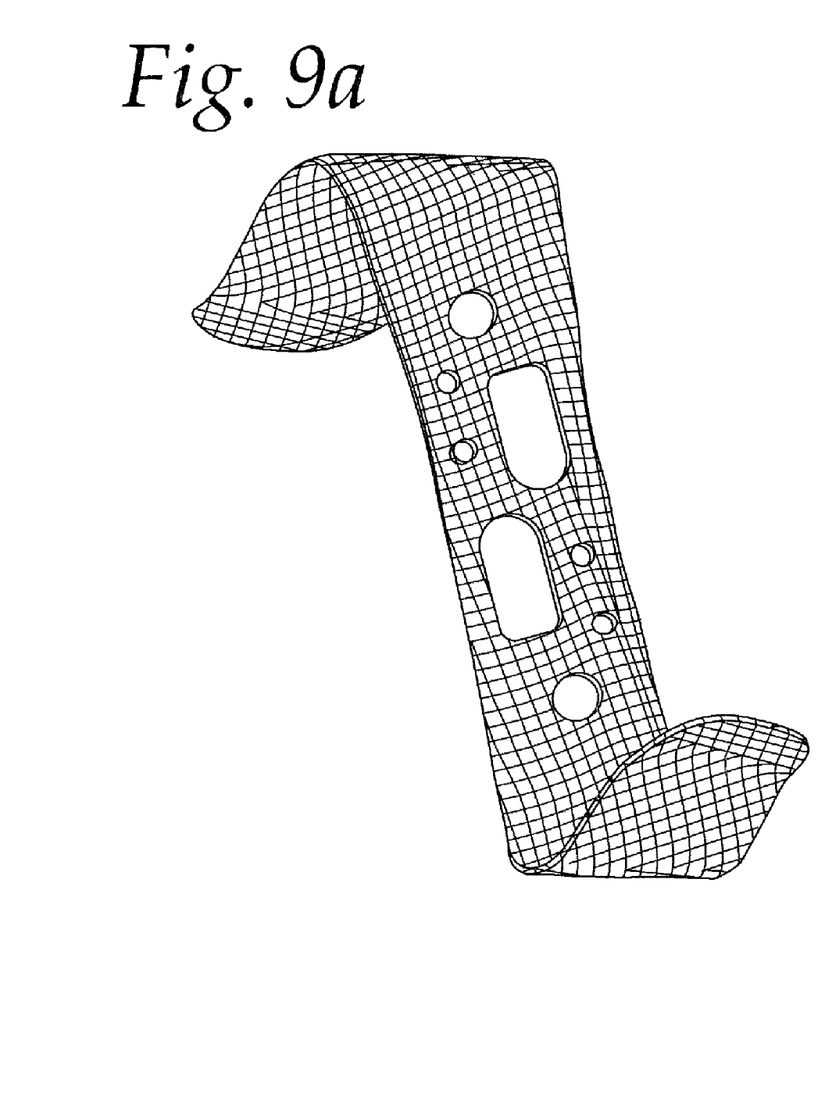
FIG. 9a is a rear view of the surgical retractor in FIG. 1a, wherein said retractor is disposable and is covered with a stainless steel mesh.
Figure 9B:
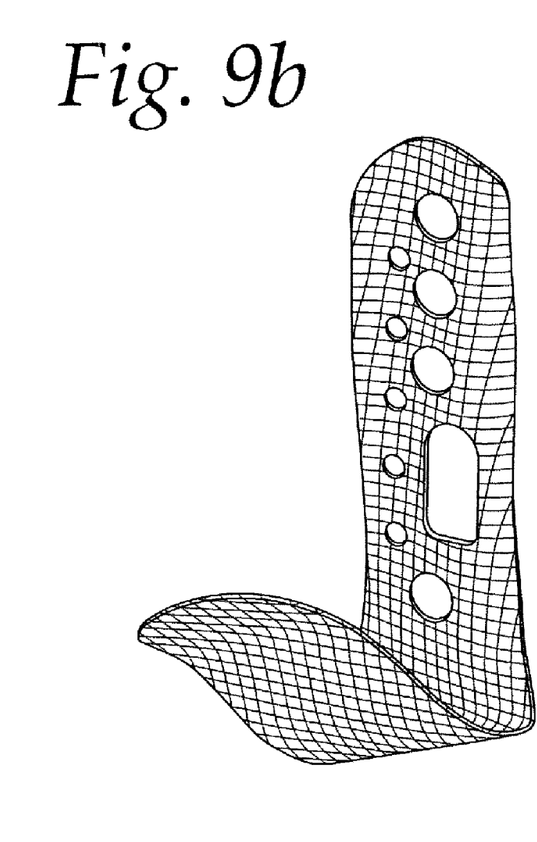
FIG. 9b is a front view of the surgical retractor in FIG. 3a, wherein said retractor is disposable and is covered with a stainless steel mesh.

In another embodiment, the retractors may be made of plastic. If the retractor is made of plastic, it preferably further comprises a stainless steel mesh which covers both surfaces of the retractor. Such stainless mesh is preferably about 0.1 mm in thickness and the size of the squares of the mesh is about 3.5 mm long. Preferably, the stainless steel mesh is thermally fused onto plastic surfaces. Some of the reasons to include the stainless steel mesh may be to increase the durability of the retractor and to prevent parts of the retractor from breaking off the retractor during surgical procedures. FIG. 9 provides an illustration of an embodiment of the present invention where the stainless steel mesh is provided on the plastic retractor. The plastic retractors may further be disposable.

FIGS. 5-8 provide further illustrations of the types of retractors encompassed by the present invention.

It is to be understood that these illustrations are not meant to limit the invention in any way, and are included solely to demonstrate possible embodiments of the invention.

Thus, the retractors according to the present invention provide convenient widely exposed retraction of the incision sites, provide less trauma to local tissue, result in a better view inside the surgical wounds or body cavities, better exposure for revision, hemostasis or other cavity manipulations. The provided retractors are effective tools for evacuation of the air, fluids, debris, smoke, and the like from the wound and body cavities. At the same time, it is possible to use the provided retractors without the suction tubes. The retractors provide for the simultaneous full length opening of the surgical wound and elevation of the wound's sectors. Accordingly, the provided retractors require significantly less efforts to achieve and retain a steady retraction for prolonged periods of time. The retractors are useful and easily adaptable to different types of surgical procedures in various surgical specialties. It is well within a skill of the art to provide the necessary changes, if any, to the provided retractors to make them suitable for a particular operation.

In yet another embodiment, the invention provides a disposable pouch for a pre-shaped breast implant, wherein said disposable pouch has at least two notches and wherein a perforated line is extended from each of said two notches. The provided pouch is preferably made of synthetic nanotech porous material. It is preferably water-repellent and is mechanically strong.

The invention encompasses different sizes of the disposable pouch; each size of the pouch can accommodate the corresponding implant with up to 50 cc difference in filling volumes.

The pouches of the invention are intended to correspond to breast implants of various sizes; it is well within of skill in the art to produce the pouches of the invention to make them correspond to an implant of any size. For example, in one preferred embodiment, the disposable pouch for an implant of about 300 cc volume is about 127 mm wide in the central part.

In another preferred embodiment, the disposable pouch comprises at least two strings which are extensions of the central body of the pouch and are made of the same material. In one embodiment, the strings are about 38 mm wide and about 70 mm long (for a pouch which corresponds to an implant of between about 275 cc and 325 cc in volume). Further, the disposable pouch preferably has at least four fabric folds on each side of the vertical midline. Even more preferably, the pouch has at least two deep notches at about the peak of the fabric curvature, and a vertical perforated line extending from each notch. The notches and the perforated line are easily separated and removed after the implant is placed in the patient's body.

One of the advantages of the disposable pouch is that it provides an extra protection to the implant's shell by helping to redistribute the applied force of negative pressure in the implantation passage and the placement pocket. It is thus an additional, protective shell which may be used as an advanced slide platform for the implant. The strings provide extra control during the implantation procedure by helping to secure the directional vector force to move the implant toward the placement pocket.

Figure 10A:
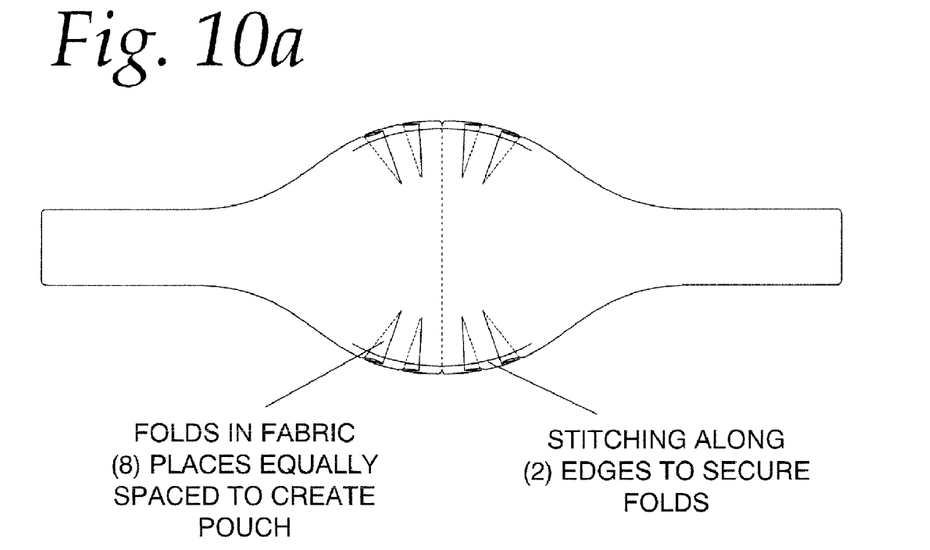
FIG. 10a is a top view of a disposable pouch for a breast implant according to another preferred embodiment of the invention.
Figure 10B:
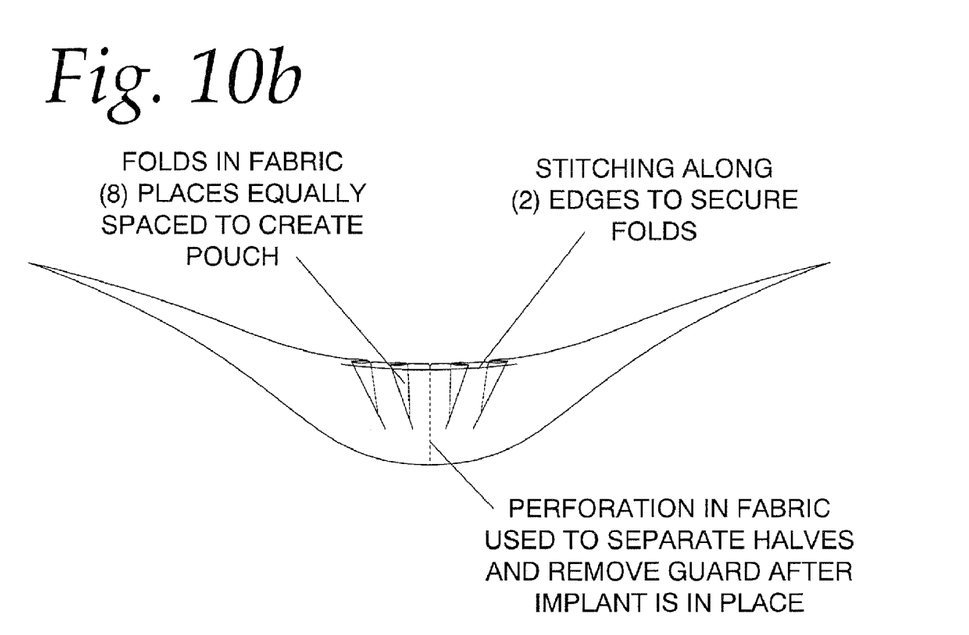
FIG. 10b is a side view of a disposable pouch for a breast implant according to another preferred embodiment of the invention.

FIG. 10a depicts a top view and FIG. 10b depicts a side view of a preferred embodiment of the pouch.

In yet another embodiment, the invention provides a method of performing a breast enhancement surgery using pre-filled implants, wherein said method comprises the use of one or both of the provided retractors and the use of a suction generating device to create a negative pressure in the placement pocket for the breast implant. Preferably, the provided method of performing a breast enhancement surgery comprises the use of the provided disposable pouch for the breast implant.

In a preferred embodiment, the method comprises the following steps:
 a) making an access incision and forming the placement pocket;
 b) placing a pre-filled (shaped) breast enlargement implant in an appropriate disposable pouch as described in the present invention;
 c) inserting either or both of the "Z-shaped" or "singular" retractors comprising a suction tube through the access incision into the implantation passage, wherein said retractor is connected to a suction generating device through the suction tube;
 d) placing the implant next to the incision site and aligning the implant with the direction of the placement, wherein about 75% of the implant is covered by the disposable pouch;
 e) activating a suction generating device and maintaining a negative pressure up to about 20 mm Hg;
 f) directing the implant into the implantation passage;
 g) when about 75% of the implant is inside the placement pocket, disengaging the suction generating device;
 h) pushing the remaining part of the implant inside the placement pocket;
 i) pulling strings of the disposable pouch apart; and
 j) removing the disposable pouch and the retractor from the implantation passage.

In addition, it is possible to use a water soluble surgical lubricant during the claimed method to lubricate the implantation passage. Lubrication can be made on the external side of the disposable pouch (toward the incision site); on the implant's surface facing the incision; and/or on the retractor's plates. The negative pressure inside the implantation cavity sucks in the implant, and thus, the lubricant will significantly lower resistance to the implant's advancement.

In a preferred embodiment, the water soluble surgical lubricant comprises hyaluronic acid. In the most preferred embodiment, the water soluble surgical lubricant is Surgilube®, which is a surgical lubricant made of natural water-soluble gums that contains the antiseptic Chlorhexidine Gluconate.

The described steps do not necessarily have to be performed in the above order. Further, it is possible to have intervening steps in between the described steps.

It is also possible to use the singular retractor(s) with and without the attached suction tube; for example, a suction tube may be attached to only one retractor. It is also possible to use the singular retractor with Z-shaped retractor with or without suction devices. When both retractors are used, they should be oriented in approximately opposite directions. This allows to achieve full retraction and to fully retract the implantation passage and the placement cavity. Also, when the retractors are placed in this fashion, they are placed along the diagonal line with respect to the longitudinal axis of the patient's body, and thus, do not interfere with the surgeons' manipulations and do not obstruct the surgical field of vision.

In a preferred embodiment, the Z-shaped retractor is used; wherein the first retractor plate (i.e., the longer plate) is used during inframammary and transaxillary incisions, while the second retractor plate is used for transareolar incisions.

In another preferred embodiment, sterile 0.9% saline solution is applied into the implantation passage before the implant is pushed inside the implantation passage.

It is within a skill of the art to modify the described methods, as needed.

As used in the specification and the claims, all numerical values relating to amounts, weight percentages, and the like are defined as "about" or "approximately" each particular value, plus or minus 10%. Therefore, amounts within 10% of the claimed values are encompassed by the scope of the claims.

As used in the specification and the claims, the singular forms "a," "an," and "the" include plural referents unless the context clearly dictates otherwise.

The above description is for the purpose of teaching the person of ordinary skill in the art how to practice the present invention, and it is not intended to detail all those obvious modifications and variations of it which will become apparent to the skilled artisan upon reading the description. It is intended, however, that all such obvious modifications and variations be included within the scope of the invention in any sequence which is effective to meet the objectives there intended, unless the context specifically indicates the contrary.

I claim:

1. A Z-shaped retractor for use in breast enhancement surgeries wherein said retractor comprises:
a handle, wherein said handle comprises at least two compartments suitable for a suction tube;
and two single retractor plate contiguous to said handle and located at the opposite ends of the handle, wherein each of the single retractor plates contains a distal end, and a proximal end directly adjoined to said handle, and, wherein each of the single retractor plates is oriented at acute angles relative to the X-axis and the Y-axis, wherein the X-axis runs along the front view of said handle, and the Y-axis runs along the side view of said handle, and wherein said acute angles are measured from the distal end of each of the single retractor plates to the X-axis and Y-axis in the direction to the opposite end of the handle, and wherein each of the single retractor plates has a first angle of said acute angles of between 20° and 40° along the Y-axis of said handle, and a second angle of said acute angles of between 25° and 45° along the X-axis of said handle; and wherein each of the retractor plates is curved in the opposite direction to the other retractor plate relative to said handle to define a Z-shape retractor.

2. The retractor of claim 1, wherein said handle is between 140 mm and 180 mm in length; between 20 mm and 40 mm in width; and between 0.5 mm and 1.5 mm thick.

3. The retractor of claim 1, wherein edges of said retractor are rounded.

4. The retractor of claim 1, wherein one of the retractor plates is between 40 mm and 60 mm in length; between 20 mm and 40 mm in width; and between 0.5 mm and 1.5 mm thick.

5. The retractor of claim 1, wherein one of the retractor plates is between 25 mm and 45 mm in length; between 16 mm and 36 mm in width; and between 0.5 mm and 1.5 mm thick.

6. The retractor of claim 1, wherein said handle further comprises a plurality of openings.

7. A retractor for use in breast enhancement surgeries wherein said retractor comprises:
a handle, wherein said handle comprises at least one compartment suitable for a suction tube; wherein said handle further comprises a plurality of openings; and
a single retractor plate contiguous to said handle, and located at one end of the handle, wherein said single retractor plate contains a distal end, and a proximal end directly adjoined to said handle, and wherein the single retractor plate is oriented at acute angles relative to the X-axis and the Y-axis, wherein the X-axis runs along the front view of said handle, and the Y-axis runs along the side view of said handle, and wherein said acute angles are measured from the distal end of the single retractor plate to the X-axis and Y-axis in the direction to the opposite end of the handle, and wherein the single retractor plate has a first angle of said acute angles of between 20° and 40° along the Y-axis of said handle, and a second angle of said acute angles of between 25° and 45° along the X-axis of said handle.

8. The retractor of claim 7, wherein said handle is between 120 mm and 140 mm in length; between 16 mm and 36 mm in width; and between 0.5 mm and 1.5 mm thick.

9. The retractor of claim 7, wherein edges of said retractor are rounded.

10. The retractor of claim 7, wherein said retractor plate is between 25 mm and 45 mm in length; between 20 mm and 40 mm in width; and between 0.5 mm and 1.5 mm thick.

11. The retractor of claim 1 or 7, wherein said retractor further comprises a suction tube.

12. A surgical kit comprising the retractor of claim 1 or 7.

* * * * *